United States Patent
Diehl et al.

(10) Patent No.: US 6,266,993 B1
(45) Date of Patent: Jul. 31, 2001

(54) METHOD FOR TESTING A MEASURING SENSOR

(75) Inventors: Lothar Diehl, Stuttgart; Alexander Bareiss, Immenstadt, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/412,868

(22) Filed: Oct. 5, 1999

(30) Foreign Application Priority Data

Oct. 6, 1998 (DE) .............................................. 198 45 927

(51) Int. Cl.⁷ ........................ G01N 27/409; G01N 27/41
(52) U.S. Cl. .................... 73/1.06; 73/1.03; 73/23.32; 204/427; 205/784.5
(58) Field of Search ..................... 73/1.02, 1.03, 73/1.06, 23.31, 23.32; 204/427; 205/784, 784.5

(56) References Cited

U.S. PATENT DOCUMENTS

| | | | |
|---|---|---|---|
| 5,080,765 | * 1/1992 | Wang et al. | 205/784 |
| 5,221,445 | * 6/1993 | Wang et al. | 204/426 |
| 5,780,710 | * 7/1998 | Murase et al. | 73/1.06 |
| 5,804,700 | * 8/1998 | Kwon et al. | 73/1.06 |

* cited by examiner

Primary Examiner—Daniel S. Larkin
(74) Attorney, Agent, or Firm—Kenyon & Kenyon

(57) ABSTRACT

In a method for testing a measuring sensor for the determination of an oxygen concentration in a gas mixture, the measuring sensor supplies a detection voltage furnished by a Nernst measuring cell and corresponding to the oxygen concentration. The detection voltage is evaluated by a circuit arrangement and is picked off between a first electrode exposed to the gas mixture and a second electrode exposed to a reference gas. The measuring sensor is heated to operating temperature. The Nernst measuring cell is exposed to a constant test voltage and a gas mixture with a well-defined oxygen concentration and a measuring current of the Nernst measuring cell is evaluated.

3 Claims, 2 Drawing Sheets

METHOD FOR TESTING A MEASURING SENSOR

FIELD OF THE INVENTION

The present invention relates to a method for testing a measuring sensor for the determination of an oxygen concentration in a gas mixture.

BACKGROUND INFORMATION

Measuring sensors are known. By determining the oxygen concentration in the exhaust gas of internal combustion engines, such measuring sensors specify the setting of a fuel-air mixture for the operation of the internal combustion engine. The fuel-air mixture can lie in the "rich" range, that is, the fuel is in stoichiometric excess, so that only a small quantity of oxygen is present in the exhaust gas in comparison to other partly unburned components. In the "lean" range, in which atmospheric oxygen predominates in the fuel-air mixture, an oxygen concentration in the exhaust gas is correspondingly high.

"Lambda probes" are known for determining the oxygen concentration in exhaust gas; these detect a lambda value >1 in the lean range, a lambda value <1 in the rich range, and a lambda value =1 in the stoichiometric range. A Nemst measuring cell of the measuring sensor supplies in known fashion a detection voltage, which is supplied to a circuit arrangement.

In a known design of the measuring sensor, one electrode of the Nernst measuring probe is exposed to the gas mixture (exhaust gas) being monitored, a second electrode to a reference gas. The electrodes here are arranged on opposite sides of a solid electrolyte. As a result of the oxygen concentration present in the gas mixture being measured, a difference in oxygen concentration arises between the electrodes. A constant current is passed through the Nernst measuring cell, so that a certain detection voltage is set up on the electrodes as a result of the difference in oxygen concentration present. If there is a rise or fall in the oxygen concentration in the gas mixture being measured, the detection voltage decreases or, respectively, increases.

It is known to fabricate such measuring sensors as "thick-film" planar broadband lambda probes. Here, the individual functional elements of the measuring sensor are arranged and structured in layers one atop another. This layer construction is obtained, for example, by film casting, stamping, screen printing, laminating, cutting, sintering, or a like method. It has turned out that reference gas can be consumed to various extents as a result of manufacturing-related contaminants in a reference compartment of the measuring sensor. Because, however, a consumption of reference air has a substantial effect on the detection voltage with regard to generating an accurate detection voltage during the intended use of the measuring sensor, measuring sensors fabricated by the same manufacturing steps are subject to a variation in their output signal.

SUMMARY OF THE INVENTION

The method according to the present invention for testing a measuring sensor offers the advantage that measuring sensors can be exactly classified after manufacturing. Because the Nernst measuring cell is exposed to a constant test voltage and a gas mixture with a well-defined oxygen concentration, and a measuring current of the Nernst measuring cell that comes into being over time is evaluated, the consumption of reference air due to contaminants in the reference compartment can be determined in a simple fashion.

By determining the contaminants in the reference compartment of the measuring sensor, which can originate, for example, from grease deposits, stamping oil, hand sweat, or the like, oxidation of this contamination upon subsequent heating, in particular in the intended use of the measuring sensor, can be predicted. The test according to the present invention very advantageously permits in-process monitoring of any reference-air consumers (contaminants) that may be present, batch release, or material selection. Any contaminants that may be present can be divided into various categories on the basis of the test current that comes about for a constant test voltage and constant oxygen concentrations of the gas mixture present. These can preferably be classified as permanent consumers and exhaustible consumers. If such reference-air consumers (contaminants) are determined, the batch tested can be selected out and declared rejected if they are classified as permanent consumers. If they are classified as exhaustible consumers, the exhaustible reference-air consumer can be eliminated, for example by "torching," so that the measuring sensors can subsequently be released for use. Further, the test for any reference-air consumers (contaminants) present makes it possible to infer any possible causes for the occurrence of these contaminants, which can be eliminated from the manufacturing process once they are known.

During the reference-air consumption test, a well-defined heat energy is applied to the measuring sensors. In this way, the later service conditions of the measuring sensor can be simulated, especially if the measuring sensors are used as lambda probes in motor vehicles for detecting the oxygen concentration in exhaust gases. Further, the ionic conductivity of the solid electrolyte is set.

DETAILED DESCRIPTION

Figure 1:
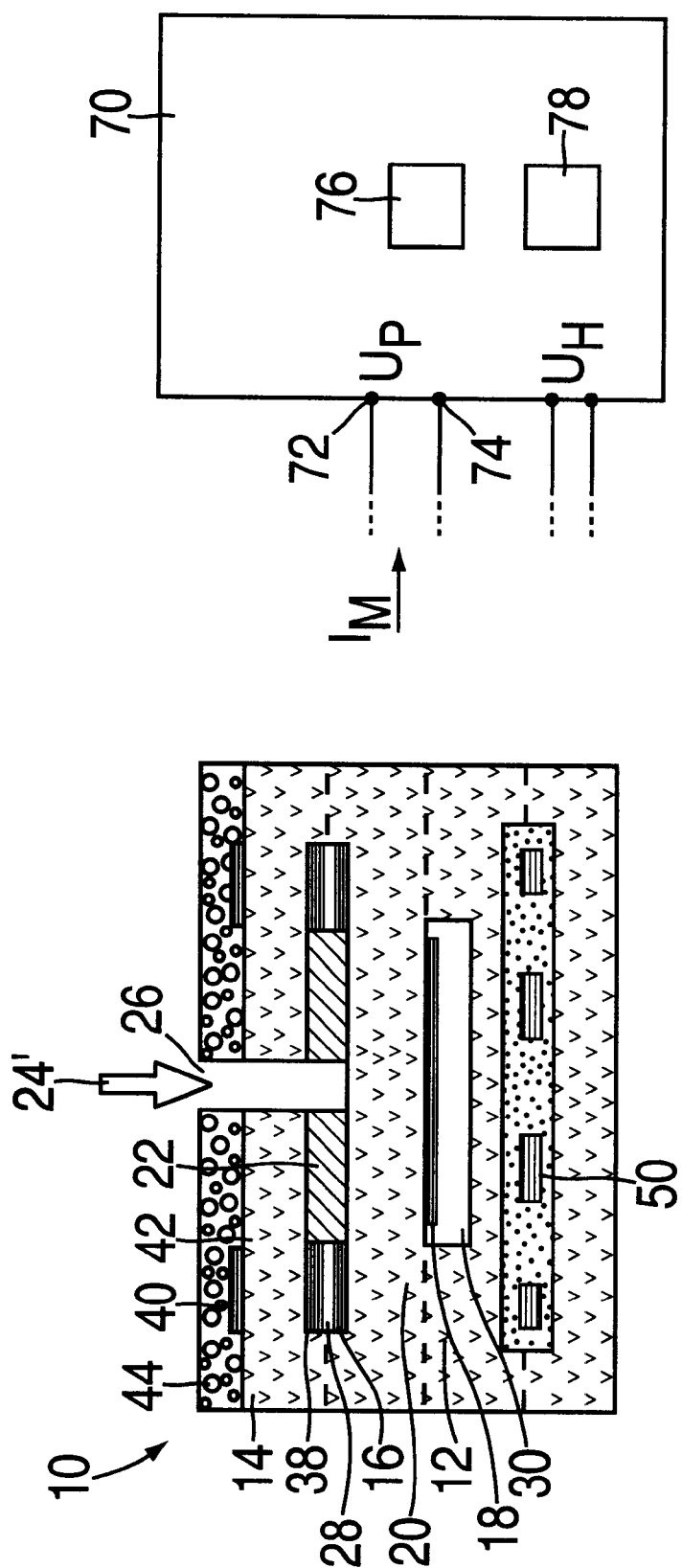
FIG. 1 shows a schematic cross-sectional view of a measuring sensor.

FIG. 1 shows a measuring sensor 10 in a cross-sectional view through a measuring head. Measuring sensor 10 is made as a planar broad-band measuring sensor and includes a number of individual layers—shown in more detail on the basis of the exploded view in FIG. 2—arranged one over another. Here the same reference symbols are used for the same parts in FIG. 1 and FIG. 2. The layered construction of measuring sensor 10 is obtained through successive structuring operations, for example by film casting, stamping, screen printing, laminating, cutting, sintering, or the like. The achievement of the layered construction will not be further discussed in the context of the present description because it is known.

Measuring sensor 10 serves to determine an oxygen concentration in gas mixtures, in particular in exhaust gases of internal combustion engines, in order to derive a control signal for the setting of a fuel-air mixture on which the internal combustion engine is operated. Measuring sensor 10 has a Nernst measuring cell 12 and a pump cell 14. Nernst measuring cell 12 has a first electrode 16 and a second electrode 18, between which a solid electrolyte 20 is arranged. Through a diffusion barrier 22, electrode 16 is exposed to the exhaust gas (gas mixture) to be measured 24. Measuring sensor 10 has a measuring opening 26, to which exhaust gas 24 can be supplied. At the base of measuring opening 26, diffusion barrier 22 extends in such a way that a cavity 28 is formed, within which electrode 16 is arranged. Electrode 18 of Nernst measuring cell 12 is arranged in a reference-air duct 30, which opens at an end of a reference-air duct film 31 distant from the measurement gas. Inside reference-air duct 30, electrode 18 is exposed to a reference gas, for example air. Solid electrolyte 20 is made, for example, of zirconium oxide stabilized with yttrium oxide, while electrodes 16 and 18 are made, for example, of platinum.

Pump cell 14 includes a first electrode 38 and a second electrode 40, between which a solid electrolyte 42 is arranged. Solid electrolyte 42 is again made, for example, of a zirconium dioxide stabilized with yttrium oxide, while electrodes 38 and 40 can again be made of platinum. Electrode 38 is likewise arranged in cavity 28 and is thus likewise exposed to exhaust gas 24 through diffusion barrier 22. Electrode 40 is covered with a protective film 44, which is porous so that electrode 40 is directly exposed to exhaust gas 24.

Measuring sensor 10 further includes a heating device 50, which is formed by a "heating meander"(folded-tape heating element). Heating device 50 is arranged between two insulating films 51 and 53, respectively, and is covered by a cover film 55.

Figure 2:
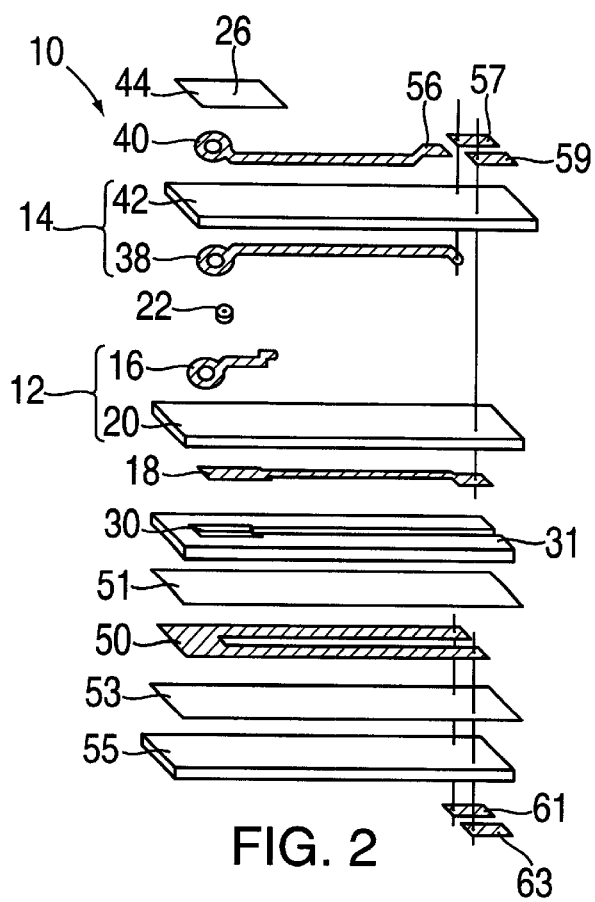
FIG. 2 shows a schematic exploded view of a measuring sensor.

As the exploded view in FIG. 2 shows, electrode 40 is connected to a terminal contact 56, electrodes 16 and 38 to a common terminal contact 57, electrode 18 to a terminal contact 59, and heating device 50 to terminal contacts 61 and 63, respectively.

Measuring sensor 10 functions in the following way.

Exhaust gas 24 passes through measuring opening 26 and diffusion barrier 22 into cavity 28 and thus to electrodes 16 of Nernst measuring cell 12 and electrode 38 of pump cell 14. As a result of the oxygen concentration present in the exhaust gas being measured, a difference in oxygen concentration comes about between electrode 16 and electrode 18, which is exposed to the reference gas. A constant current is passed through Nernst measuring cell 12 by a control device, not shown. Because of a difference in oxygen concentration present, a certain detection voltage $U_D$ is produced at electrodes 16 and 18. Nernst measuring cell 12 functions as a lambda probe, which detects whether a high oxygen concentration or a low oxygen concentration is present in exhaust gas 24. On the basis of the oxygen concentration, it is clear whether the fuel-air mixture on which the internal combustion machine is being operated is a rich or a lean mixture. Upon a change from the rich to the lean range or vice versa, detection voltage $U_D$ decreases or increases, respectively.

With the aid of the control device, not shown, the detection voltage $U_D$ is used to determine a pump voltage $U_p$ to be applied to pump cell 14 between its electrodes 38 and 40, respectively. Pump voltage $U_p$ is negative or positive, depending on whether detection voltage $U_D$ conveys a signal that the fuel-air mixture lies in the rich or lean range, so that electrode 40 functions as either cathode or anode. A pump current $I_p$ is correspondingly generated; it can be measured with a measuring device of the control device. Oxygen ions are pumped either from electrode 40 to electrode 38 or vice versa with the help of pump current $I_p$. The measured pump current $I_p$ serves to drive a device for setting the fuel-air mixture on which the internal combustion engine is operated.

A heating voltage $U_H$ can be applied to circuit arrangement 50, so that heating device 50 can be turned either on or off, respectively. Heating device 50 can bring measuring sensor 10 to an operating temperature higher than approximately 300° C.

In what follows, it is assumed that measuring sensors 10 are manufactured by mass production and that fluctuating process conditions and/or fluctuating material properties cause measuring sensors 10 to be obtained with nonidentical characteristics. This variation of the characteristics of measuring sensors 10 is caused, in particular, by different reference-air consumption of individual elements of measuring sensor 10. In order that the manufactured measuring sensors 10 can be classified in selectable categories, each of which exhibits only a maximum variation of the characteristics, these measuring sensors 10 are tested with the test method according to the present invention, which is explained in what follows.

During the testing of measuring sensors 10, they are brought into contact with a measuring gas 24' that has a known, well-defined oxygen concentration. Simultaneously, a well-defined test voltage $U_p$ is applied to electrodes 16 and 18 of Nernst measuring cell 12 via a test device 70. The test voltage is to be chosen such as the Nernst voltage would be for the concentration relationship between measuring gas 24' and the reference-gas compartment. For this purpose, electrodes 16 and 18 are connected to inputs 72 and 74, respectively, of test device 70. A measuring device 76 here measures a current $I_M$ flowing via Nernst measuring cell 12. The current $I_M$ measured by measuring device 76 is evaluated by a time-function element 78. This evaluation is based on the fact that the oxygen concentration in measuring gas 24', as a rule air, is known. Further, the oxygen concentration of the reference gas in reference-gas duct 30, also air at the start of the measurement, is likewise known. A difference in oxygen concentration at electrode 16 and electrode 18 of Nernst measuring cell 12 is likewise known. If now, while measuring gas 24' is held identical, oxygen is consumed inside reference-air duct 30, there is a compensatory (replenishing) pumping of oxygen by Nernst measuring cell 12 from electrode 16 through solid electrolyte 20 and electrode 18 into reference-air duct 30. In this way, as a consequence of the constant test voltage $U_p$ still applied, the current $I_M$ detected by measuring device 76 changes. Current $I_M$ is proportional to the oxygen consumption in reference-air duct 30.

Figure 3:
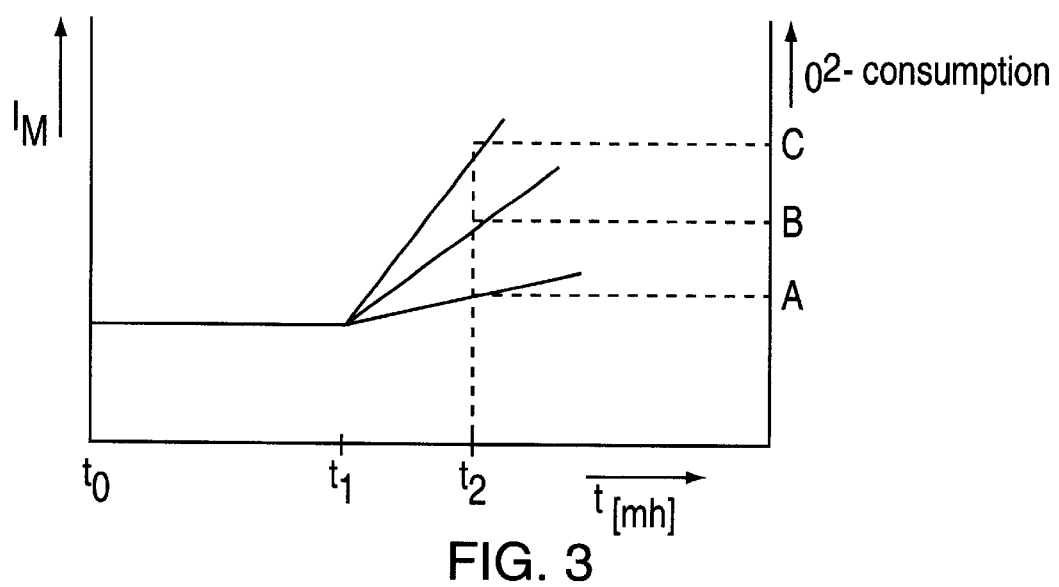
FIG. 3 shows various characteristics of the testing of measuring sensors.

This test method will be explained on the basis of the characteristics in FIG. 3. Here the measured current $I_M$ and the oxygen consumption, which is proportional to the measured current I, are plotted versus time t. The current I is measured starting at time $t_0$. Because of the initially known and constant oxygen concentration relationship, the current I will be substantially constant up to a time $t_1$,; if there is no $O_2$ consumption, the current is zero, and the only current flowing is the measuring current of the voltmeter, corresponding to the internal resistance of the measuring device. Starting at time $t_1$, which is, for example, around fifteen minutes, the oxygen concentration in reference-air duct 30 begins to decline, so that a corresponding compensatory pumping of oxygen from measuring gas 24' takes place. This decrease of oxygen gas in reference-air duct 30 depends on the oxygen uptake of the individual elements of measuring sensor 10. The decrease of the oxygen concentration in reference-air duct 30 will differ if measuring sensors 10 are nonidentical, so that the quantity of compensatory oxygen pumped from measuring gas 24' via Nernst measuring cell 12 will differ.

Corresponding to this compensatorily pumped oxygen concentration, the current $I_M$ will differ. In FIG. 3 this is indicated by a family of curves beginning at time $t_1$. Each of the curves in the family of curves stands for another measuring sensor 10. Now the current $I_M$ is measured at a time $t_2$ and converted to a proportional oxygen consumption A, B, or C, respectively. Any contaminants in reference-air duct 30 can be inferred from the measured consumption of reference air. In this way, in particular, manufacturing problems leading to manufacturing-related contaminants in reference-air duct 30 can be detected. All in all, in-process monitoring can be implemented in this way and, at the same time, batch release of tested measuring sensors 10 can be carried out, or, respectively, the tested measuring sensors can be declared rejected if nonconsumable contaminants are detected.

According to a further test method, the current $I_M$ can be measured over a time interval $t_1$ to $t_2$ and the integral of the current measured over the interval $t_1$ to $t_2$ can be used for classification into batches or, respectively, categories A, B, C, and so forth.

Further, measuring sensor 10 is heated to operating temperature during the test in order to facilitate the ionic conductivity of solid electrolyte 20. This can be done, for example, by applying a heating voltage $U_H$ to heating device 50.

What is claimed is:

1. A method for testing a measuring sensor to determine an oxygen concentration in a gas mixture, the measuring sensor supplying a detection voltage furnished by a Nernst measuring cell and corresponding to the oxygen concentration, the Nernst measuring cell including a first electrode and a second electrode, the method comprising the steps of:

heating the measuring sensor to an operating temperature;

exposing the Nernst measurement cell to a constant test voltage and to a gas mixture having a well-defined oxygen concentration;

evaluating a measuring current of the Nernst measuring cell;

picking off the detection voltage between the first electrode exposed to the gas mixture and the second electrode exposed to a reference gas; and evaluating the detection voltage using a circuit arrangement.

2. The method according to claim 1, further comprising the step of measuring the current at a preselected time instant.

3. The method according to claim 1, further comprising the steps of:

measuring the current over a preselected time interval; and determining an integral of a rise in the current.

* * * * *